(12) United States Patent
Wassenburg et al.

(10) Patent No.: US 10,856,725 B2
(45) Date of Patent: Dec. 8, 2020

(54) TIP PROTECTOR DEVICE

(71) Applicant: Wassenburg Medical B.V., Dodewaard (NL)

(72) Inventors: Ronald Wassenburg, Dodewaard (NL); Marije Anne Sijke Visschers E/V Faazen, Bemmel (NL)

(73) Assignee: WASSENBURG MEDICAL B.V., Dodewaard (NL)

( * ) Notice: Subject to any disclaimer, the term of this patent is extended or adjusted under 35 U.S.C. 154(b) by 51 days.

(21) Appl. No.: 16/347,761

(22) PCT Filed: Nov. 2, 2017

(86) PCT No.: PCT/NL2017/050706
§ 371 (c)(1),
(2) Date: May 6, 2019

(87) PCT Pub. No.: WO2018/084703
PCT Pub. Date: May 11, 2018

(65) Prior Publication Data
US 2019/0313889 A1    Oct. 17, 2019

(30) Foreign Application Priority Data
Nov. 4, 2016   (NL) ..................................... 2017723

(51) Int. Cl.
*B65D 83/10*      (2006.01)
*A61B 1/00*       (2006.01)
(Continued)

(52) U.S. Cl.
CPC .......... *A61B 1/00144* (2013.01); *B65D 85/54* (2013.01); *A61B 2090/701* (2016.02)

(58) Field of Classification Search
CPC ... B65D 85/54; A61B 1/00137; A61B 1/0014; A61B 1/00177; A61B 1/0615; A61B 1/0676; A61B 1/00144; A61B 2090/701
(Continued)

(56) References Cited

U.S. PATENT DOCUMENTS

| 6,186,325 B1 * | 2/2001 | Schmidt | A61M 25/002 206/364 |
| 6,439,276 B1 * | 8/2002 | Wood | A61M 5/1782 141/27 |

(Continued)

FOREIGN PATENT DOCUMENTS

| JP | 2007/075281 | 3/2007 |
| JP | 2007/330421 | 12/2007 |
| JP | 2013/085653 | 5/2013 |

OTHER PUBLICATIONS

Schindler, Martin, International Search Report, European Patent Office, dated Mar. 6, 2018.

*Primary Examiner* — Luan K Bui
(74) *Attorney, Agent, or Firm* — Emerson, Thomson & Bennett, LLC; Roger D. Emerson

(57) ABSTRACT

The present invention relates to a tip protector device for a medical instrument, such as an endoscope or borescope. The tip protector device according to the present invention comprises a housing configured to releasably receive a tip of a medical instrument, a clamping system configured to retain by clamping the tip received by the housing in a retaining position and a locking system configured to perform a locking step, wherein the locking step comprises, successively, the locking and unlocking of the clamping system in the retaining position. The tip protector further comprises a blocking element, wherein the blocking element is configured to block the locking system after repeated use
(Continued)

of the device. The present invention also relates to a method of protecting the tip of a medical instrument.

20 Claims, 14 Drawing Sheets

(51) Int. Cl.
*B65D 85/00* (2006.01)
*A61B 90/70* (2016.01)
(58) Field of Classification Search
USPC .......... 206/363–366, 438; 600/121, 125, 127
See application file for complete search history.

(56) References Cited

U.S. PATENT DOCUMENTS

| | | | | |
|---|---|---|---|---|
| 9,829,113 | B2* | 11/2017 | Brugger | A61M 39/284 |
| 2010/0249510 | A1* | 9/2010 | Yamada | A61B 1/00142 |
| | | | | 600/121 |
| 2012/0035553 | A1* | 2/2012 | Lombardo | A61M 39/284 |
| | | | | 604/250 |
| 2012/0232497 | A1* | 9/2012 | Singh | A61M 39/284 |
| | | | | 604/250 |
| 2013/0233746 | A1 | 9/2013 | Mason | |
| 2014/0343361 | A1* | 11/2014 | Salman | A61B 1/0014 |
| | | | | 600/125 |
| 2017/0224191 | A1* | 8/2017 | Ramsey | A61B 1/00144 |

* cited by examiner

TIP PROTECTOR DEVICE

TECHNICAL FIELD

The present invention relates to a tip protector device for a medical instrument, such as an endoscope or borescope. The present invention further relates to a method of protecting the tip of a medical instrument.

BACKGROUND

A tip protector device for instruments such as an endoscope or borescope is known in the art. International patent application WO 2016/59383 A2 describes a tip protector device comprising a guard portion engagable with a tip of an instrument, the guard portion including an abutment surface arranged to contact the tip such that a part of the guard portion extends distally of an end face of the tip, and the guard portion being configured to prevent contact between the guard portion and a central portion of the end face; gripping members arranged to grip a part of a shaft of the instrument; a first connection member; and a second connection member, the first and second connection members being movable relative to each other between a first, disengaged position in which the tip of the instrument can be inserted into and removed from the tip protector device, and a second, gripping position in which the gripping members contact and grip the shaft of the instrument, wherein, the first and second connection members are biased in the first or the second position.

The tip protector device disclosed in the prior art is suitable for a single use, i.e. protecting the tip of clean and disinfected instrument, removing the tip protector device from the tip before use and after use protecting the tip of the instrument with the same tip protector device. The tip protector device disclosed in the prior art is provided with distinguishing means to allow the user to determine whether the tip protector has been engaged with a 'clean' or 'dirty' instrument. To this end a removable tab is attached to a connecting member, wherein the tab provides a first distinguishing means (i.e. 'clean') and wherein the tab is configured such that by removal of the tab a second distinguishing means (i.e. 'dirty') is revealed.

The present invention, however, provides a tip protector device for a medical instrument comprising a housing configured to releasably receive a tip of a medical instrument, a clamping system configured to retain by clamping the tip received by the housing in a retaining position, and a locking system configured to perform a locking step, wherein the locking step comprises, successively, the locking and unlocking of the clamping system in the retaining position. The tip protector device of the present invention differs from the tip protector device disclosed in the art in that the locking system of the tip protector device of the present invention further comprises a blocking element, wherein the blocking element is configured to block the locking system after repeated use of the tip protector device.

By providing a locking system which is able to perform multiple locking steps, the tip protector device of the present invention can be used throughout the reprocessing cycle of a medical instrument, such as an endoscope or borescope. The reprocessing cycle of a medical instrument comprises several steps wherein the repeated use of the tip protector device, i.e. repeated locking and unlocking of the tip protector device, is desired to protect the tip of a medical instrument throughout the reprocessing cycle, thus not only during transport of the medical instrument from the clean room to the treatment room and from the treatment room to the dirty room, but also during transport of the medical instrument between the several steps performed within, mainly, the clean room and the dirty room, e.g. including the washing and disinfection of the medical instrument and/or the drying of the medical instrument. By providing a locking system comprising a blocking element, which blocking element is configured to block the locking system by the end of the reprocessing cycle of a medical instrument, the present invention provides a robust and safe-to-use tip protector device. By blocking the locking system permanently using the blocking element of the present invention, the user is not able to re-use a tip protector device already engaged with a dirty tip with a tip of a cleaned and disinfected medical instrument.

The present invention thus provides a tip protector device wherein the tip protector device is suitable for repeated use, i.e. repeated locking and unlocking of the tip protector device, before the tip protector device is disabled for further use. By disabling the tip protector device of the present invention after a predefined number of locking steps, the tip protector device of the present invention provides a self-regulating tip protector device. In other words, any re-use of a dirty tip protector device as a consequence of inconsideration, carelessness or imprudence by the user, is avoided by providing the locking system of the present invention.

In an embodiment of the present invention, the locking system is configured to perform at least a first and a second locking step before the blocking element blocks the locking system. In this way the user is able to protect the tip of a clean and disinfected medical instrument and transporting the medical instrument to the treatment room. After unlocking and use of the medical instrument, the user is able to protect the dirty tip of the medical instrument again with the tip protector device. After transporting the dirty medical instrument to the dirty room for further cleaning and disinfection, the user is able to unlock the tip protector device whereby at the same time the locking system is blocked by the blocking element for further use.

In another embodiment of the present invention, the locking system is further configured to perform a third locking step before the blocking element blocks the locking system. In this way the user is able to perform an additional locking step in addition to the steps described above, i.e. protecting the tip of a medical instrument during the transportation of the medical instrument from the clean room to the treatment room and from the treatment room to the dirty room. Preferably, the additional step is performed in the dirty room, i.e. during the first step in the reprocessing cycle of a medical instrument. For example, the tip protector device of the present invention may be provided with means for receiving spare parts of a medical instrument, such as valves to be cleaned of a used medical instrument. By providing such a tip protector device the user is able to insert the valves into the tip protector device and placing the tip protector device together with the corresponding medical instrument in a washer and disinfector for medical instruments. After washing and disinfecting the medical instrument, the corresponding tip protector device, comprising the valves of the cleaned and disinfected medical instrument, is engaged with the tip of the medical instrument. Alternatively, the tip protector device comprising the spare parts may be engaged with the tip of the medical instrument before performing washing and disinfecting the medical instrument. By providing a tip protector device wherein additional locking steps are allowed, the user is able to perform multiple steps during the medical instrument reprocessing cycle wherein the medical instrument, any particular spare parts of the medical instrument and the tip protector device are interconnected throughout the reprocessing cycle.

Given the above, the tip protector device of the present invention thus provides a multifunctional device which can be used throughout a medical instrument reprocessing cycle without the need of additional storage devices such as the storage device disclosed in International patent application WO 2012/056206 A1.

SUMMARY

The locking system of the present invention may comprise any locking mechanism which is able to perform multiple locking steps. Preferably, the locking system is configured such that the user is able to visually detect the actual 'status' of the tip protector device. By providing indication means, such as colours corresponding to the 'traffic light' principle, the user is able to detect whether the medical instrument engaged with the tip protector device is clean ('green') or dirty ('yellow') and whether the tip protector is disabled for further use ('red'). Alternatively or in combination, the indication means may include written text, such as 'clean', 'dirty' and 'discard'/'dispose'.

It is noted that the locking system is preferably configured such that the locking system functions corresponding to the 'one-way-street' principle, i.e. once the locking system is activated by the user (e.g. by performing the first locking step) the user is not allowed to undo the steps performed. In other words, the user is only allowed to perform the next step of the locking system. Thus, by providing a locking system wherein the number of steps are predefined before disabling the locking system, i.e. by activating the blocking element, a robust and simple system is provided wherein the tip protector device is used in a safe and correct way and wherein the tip protector device is disposed after use.

A preferred locking system comprises a slide switch system. Such slide switch system provides a robust locking system, since such system may be designed such that the user is only able to move the switch in a first direction, and wherein the slide switch system is designed to block the movement of the switch in a second direction. By providing a slide switch system wherein the slide switch system comprises plural predefined positions, wherein each of the predefined positions provides a locking step or unlocking step, the user is able to perform a sequence of locking steps without the necessity to remember the previous steps performed. Thus, the risk of the omission or repetition of a locking step during the reprocessing cycle is reduced to the absolute minimum.

Alternatively, the locking system may comprise other kinds of locking mechanisms including, for example, a click mechanism, e.g. like a click mechanism of a mechanical pencil. Such click mechanism is configured such that the use is able to perform a predefined number of 'clicks' before the blocking element blocks the click mechanism and thus disabling the user to perform further 'clicks'.

The locking system of the present invention may be configured to manually lock and unlock the clamping system in the retaining position. Preferably, the locking system of the present invention may be configured to automatically lock the clamping system in the retaining system by closure of the clamping system, i.e. bringing the clamping system into clamping position, and manually unlock the clamping system in the retaining position. In such way, the user is able to bring the clamping system into clamping position without the further need of physically performing a locking step, i.e. locking the tip protector device to maintain the retaining position (clamping position).

The clamping system of the present invention may comprise one or more clamping elements. In an embodiment of the present invention, the clamping elements cooperate with the housing of the tip protector device, i.e. form an integral part of the housing of the tip protector device.

Further, the clamping system may comprise one pair of cooperating clamping elements. The clamping elements are preferably configured such that the clamping elements retain by clamping the tip under pre-tension. By providing clamping elements that retain the tip by clamping under pre-tension, the tip of the medical instrument is gently clamped without the risk of damaging the tip of the medical instrument on one hand, and without the risk of unwanted disengagement of the tip protector device from the tip of the medical instrument. The clamping elements may be designed such that the clamping force applied to the tip of the medical instrument is increased in the event the tip protector device and a clamped tip of the medical instrument are moved away from each other. The clamping elements may be designed such that no clamping force is experienced by the user in case the tip protector device and the clamped tip of the medical instrument are moved towards each other. Suitable clamping elements may include flexible clamping lamellae, e.g. clamping 'fingers' arranged in a cone-shaped structure, wherein the (imaginary) apex of the cone is facing away from a tip receiving opening provided in the housing of the tip protector device.

Given the above, in the embodiment of the present invention, the clamping elements may be configured such that the tip protector device may be locked first, before engaging the tip protector device with the tip of a medical instrument. By providing clamping elements which provide a clamping force only in case the tip protector device and a clamped tip of the medical instrument are moved away from each other, the tip protector device of the present invention still provides a robust and reliable way of performing the predefined sequence of locking steps. For such tip protecting device, the unlocking of the locking system is required to remove the tip protector device from the tip of the medical instrument.

The housing of the tip protector device of the present invention may comprise through-holes to allow easy cleaning and disinfecting of the medical instrument, and optional further spare parts of the medical instrument, such as valves of an endoscope or borescope. As already stated above, the housing comprises an opening for receiving the tip of the medical instrument. The housing may comprise a cylindrical jacket, the jacket comprising an open end configured to receive a tip of a medical instrument and a closed end located opposite the open end. It is noted that the term 'receiving' as used in this respect is not limited to mean an opening provided in the housing that is suitable for inserting the tip of the medical instrument. Alternatively the housing of the present invention may be designed such that the tip of a medical instrument is positioned in a first part of the housing. By covering the tip by a second part of the housing, the housing of the tip protector device of the present invention is formed. In order to increase the efficiency of the cleaning and disinfecting of the tip of the medical device as well as during drying of the cleaned and disinfected medical instrument, the closed and of the jacket preferably comprises through-holes.

The tip protector device of the present invention may be designed to combine different functionalities into one single device. In this respect the tip protector device of the present invention may further comprise at least one receiving means configured to releasably receive at least one spare part of a medical instrument. In a preferred embodiment the at least one receiving means is configured to receive by clamping the at least one spare part.

Although the locking system of the present invention may be configured to, successively, locking and unlocking of the at least one spare part received by the at least one receiving means, the receiving means may comprise a disconnecting element for detaching from the at least one receiving means the at least one spare part coupled with the receiving means. In this way, the user is able to unlock the tip protector device without the undesired release of the at least one spare part from the receiving means.

In an alternative embodiment of the present invention, the locking system may be configured such that the locking system is able to perform one or more locking steps only after the at least one receiving means receive at least one spare part. In other words, by receiving at least one spare part by the receiving means, the locking system is activated and ready for use.

With regard to the disconnecting element, it is noted that the disconnecting element may be further configured to block the at least one receiving means for receiving spare parts of a medical instrument after activation of the disconnecting element. Repeated use of the receiving means is herewith prevented.

The housing is preferably made from a single piece of material. The material is preferably selected from plastic, more preferably a semi-flexible plastic. By providing a housing made of semi-flexible plastic, not only the housing is able to absorb external impact without damaging the housing, the use of any hinges (and additional materials) may be avoided. Therefore, further simplifying the design of the tip protector device and, consequently, further reducing possible contamination of the tip protector device during use.

In an embodiment of the present invention the tip protector device may comprise a housing formed by a first housing part and a second housing part, wherein at least the first housing part or the second housing part comprises the clamping system configured to retain by clamping the tip of a medical instrument received by the housing and the first housing part and the second housing part are hingedly connected to each other. Again it is emphasized that the hinged connection between the first and second part of the housing may be formed by a weakened line in the material forming the housing. Alternatively the hinged connection may be formed by a part of the housing wherein the material the housing is made from is able to bend. Preferably, the first housing part and the second housing part are hingedly connected to each other such that both housing parts form the housing under pre-tension. In such way, the housing of the tip protector device of the present invention is in open position by default. In other words, once the retaining position is unlocked by the user, the housing parts will automatically move away from each other allowing the user to easily remove the tip of the medical instrument from the tip protector device.

The first housing part and the second housing part may both comprise the clamping system configured to retain by clamping the tip of a medical instrument received by the housing. In such way, the housing part is able to receive a tip of a medical instrument by the first housing part, which tip is clamped by the tip protector device once the second part is brought into connection with the first part to form the housing.

The locking system of the present invention may be comprises in the first housing part and/or the second housing part. Further, the first housing part and/or the second housing part may comprise one or more receiving means, said receiving means are configured to releasably receive at least one spare part of a medical instrument.

The present invention further relates to a method for protecting a tip of a medical instrument, comprising the steps of: a) providing a medical instrument, such as an endoscope or borescope; b) providing the tip protector device of the present invention; c) inserting the tip of the medical instrument in the tip protector device, such that the tip is retained by clamping by the tip protector device in a locked retaining position; d) unlocking the retaining position and removing the tip from the tip protector device; e) after use of the medical instrument, inserting the tip of the medical instrument in the tip protector device such that the tip is retained by clamping by the tip protector device in a locked retaining position; and f) unlocking the retaining position and removing the tip from the tip protector device, with the proviso that the method excludes the step of using the medical instrument within or on the human or animal body.

The method of the present invention further comprises the step of after unlocking the retaining position in step f), discarding the tip protector device in a suitable waste container.

The method of the present invention may further comprise the step of, between step c) and step d), transporting the medical instrument.

The method of the present invention may further comprise the step of, in step c) and step e), automatically or manually locking the retaining position. The locking of the retaining position may be performed either before or after insertion of the tip of the medical instrument in the tip protector device.

Further, the method of the present invention may comprise, between step b) and step c), washing and disinfecting the medical instrument provided in step a) and the tip protector device provided in step b). Optionally, but not necessarily, the method of the present invention may further comprise, between step c) and step d), drying the resulting assembly of step c), said assembly comprising the medical instrument provided in step a) and the tip protector device provided in step b). In this way, the present invention provides a method wherein the tip protector device can be used throughout the whole reprocessing cycle of a medical instrument. Although, after the washing and disinfecting step, direct use of the washed and disinfected assembly of the medical instrument and the tip protector device is possible, it is even possible to store the washed and disinfected assembly for later use, without running the risk of contamination or damaging of the tip of the medical instrument stored.

In case spare parts of the medical instrument needs to be connected to the medical instrument during processing of the medical instrument, the method of the present invention further comprises the steps of: i) providing at least one spare part of the medical instrument provided in step a); ii) receiving in the tip protector device provided in step b) the at least one spare part provided in step i; and iii) removing in step d) the at least one spare part from the tip protector device.

In a preferred embodiment of the method of the present invention, step ii is performed between step b) and step c)

before washing and disinfecting the resulting assembly of step c), said assembly comprising the at least one spare part provided in step i of the medical instrument provided in step a) and the tip protector device provided in step b). The present invention thus provides a method wherein the spare parts of the medical instrument are washed and disinfected together with the tip protector device of the present invention. By placing the tip protector device in a washer and disinfector for medical instruments together with the spare part related medical instrument, the risk of losing spare parts during the washing and disinfection, and if applicable, during drying of the medical instrument is further decreased.

BRIEF DESCRIPTION OF THE DRAWINGS

The invention will now be elucidated into more detail with references to the following figures, in which.

DETAILED DESCRIPTION

Figure 1A:
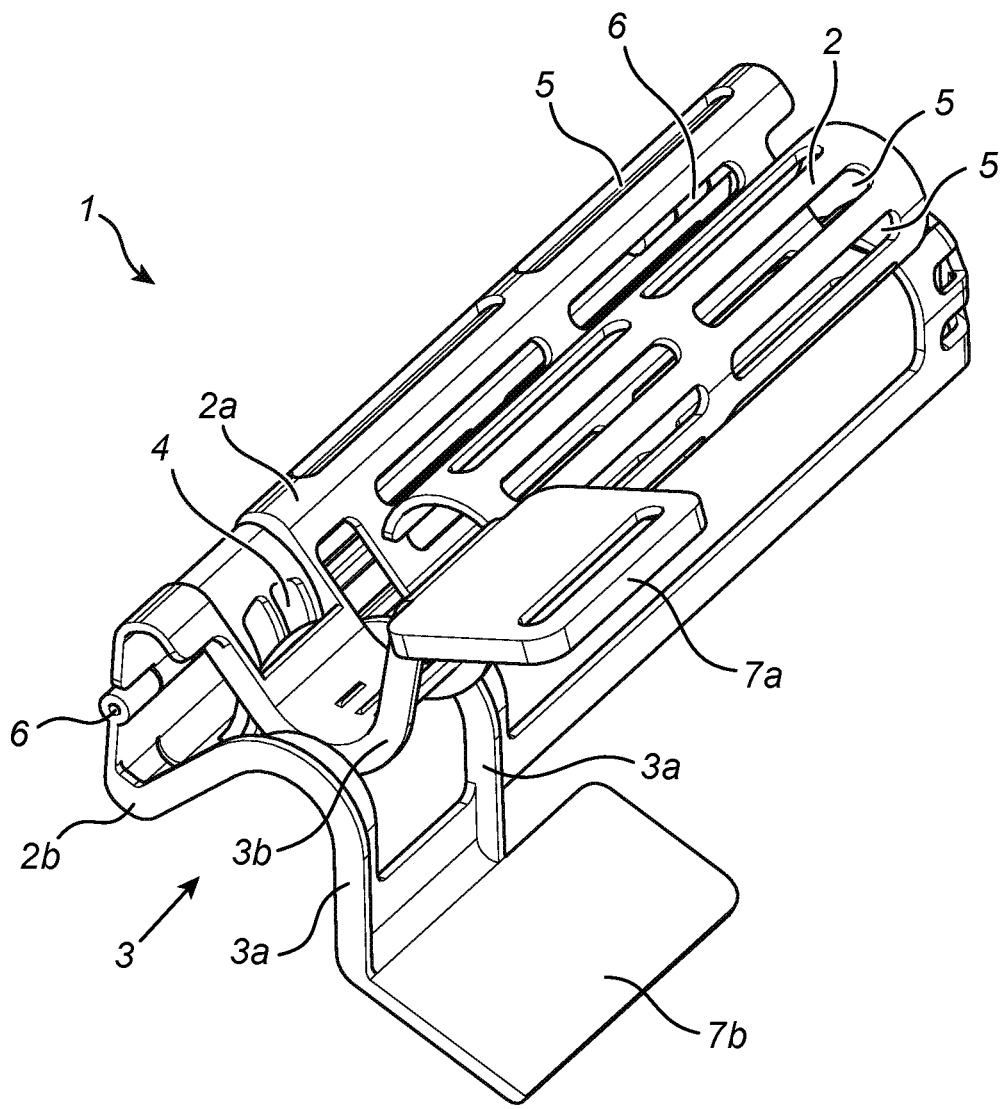
FIG. 1A-1C shows a perspective view of a first embodiment of the tip protector device of the present invention.

FIG. 1 shows a tip protector device 1 of the present invention comprising a housing 2, a clamping system 3 and a locking system 4. The housing 2 is provided with multiple through-holes 5. The housing 2 comprises a first housing part 2a and a second housing part 2b hingedly connected via couplings 6. The locking system 4 includes a click mechanism which is operated by pressing parts 7a and 7b. FIG. 1 shows the tip protector device 1 in inactive state, i.e. the initial state of the tip protector device 1 before receipt of the tip of a medical instrument.

Figure 1B:
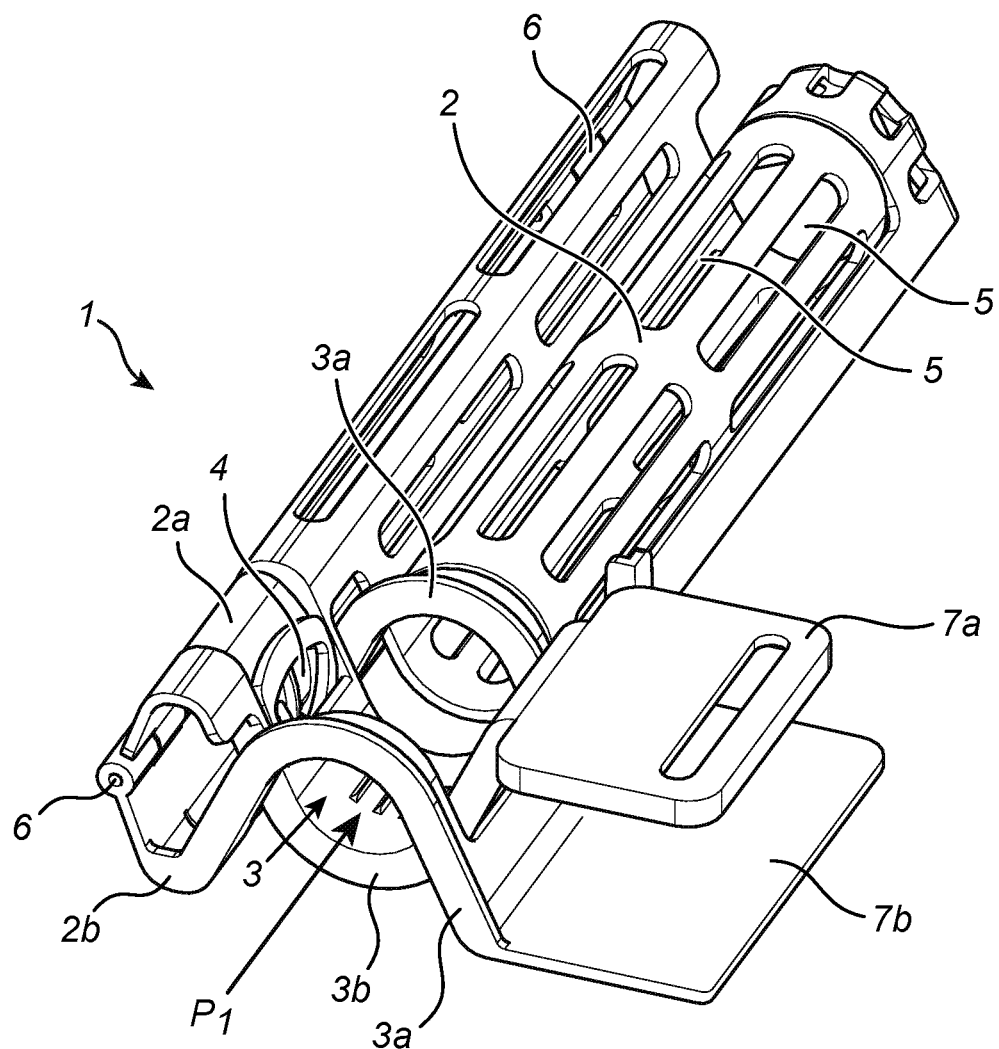

In order to receive a medical instrument, reference is made to FIG. 1B wherein the same tip protector device 1 is shown but wherein the pressing parts 7a and 7b have been moved toward each other (under pre-tension caused by the hinged connection 6 of both housing parts 2a, 2b). The medical instrument (not shown) can now be introduced in the direction of arrow P1. Once the tip of the medical instrument is inserted into the housing 2, the pressure applied by the user to pressing parts 7a, 7b is removed, resulting in the clamping elements 3a and 3b to move toward each other, clamping the tip of the medical instrument inserted into the housing 2. The tip of the medical instrument can be removed from the housing by moving the pressing parts 7a, 7b towards each other.

Figure 1C:
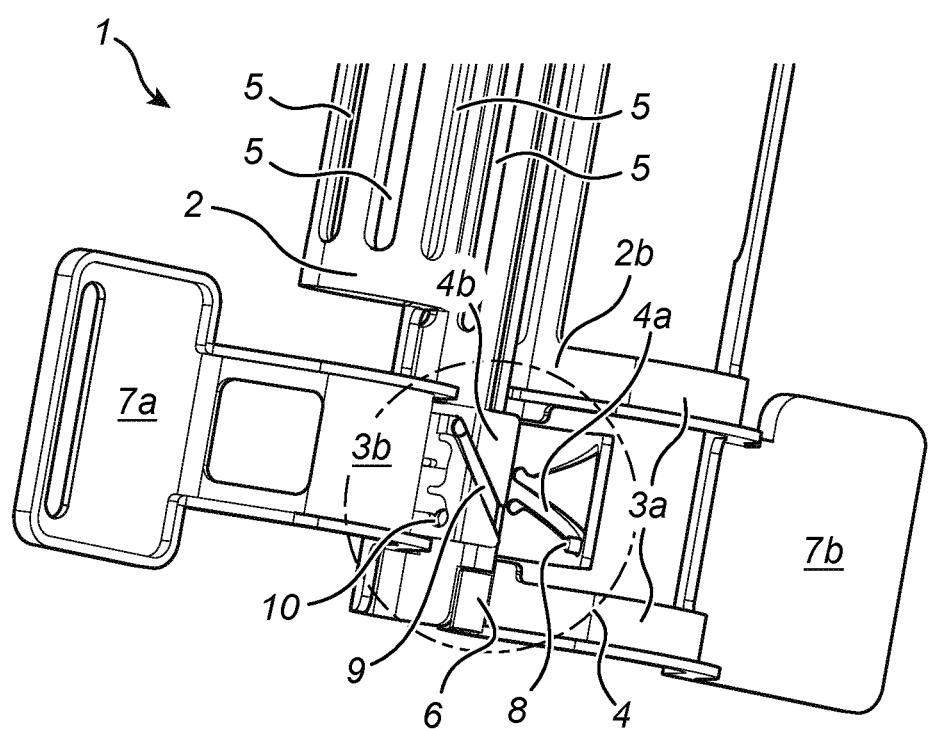

The locking system 4 of the tip protector device 1 of FIG. 1 is further elucidated into more detail in FIG. 1C. The locking system 4 comprises a flexible locking element 4a and a guiding element 4b. The flexible locking element 4a cooperates with the guiding element 4b when the tip protector device 1 is in active position (see: configuration of FIGS. 1A and 1B). The guiding element 4b is designed such to provide a limited number of predefined locking and unlocking positions. The locking element 4a comprises a protruding part 8. The protruding part 8 is guided throughout the guiding path 9 of the guiding element 4b, and after completion of the path 9 locked in final position 10.

Figure 2A:
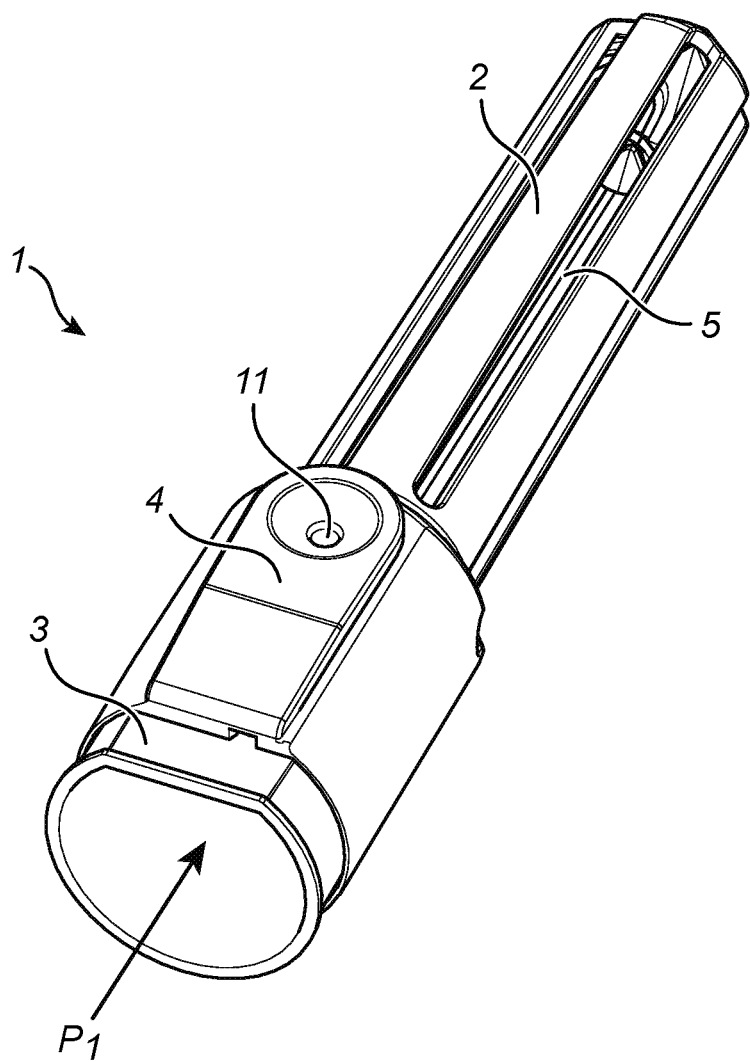
FIG. 2A-2B shows a perspective view of a second embodiment of the tip protector device of the present invention.
Figure 2B:
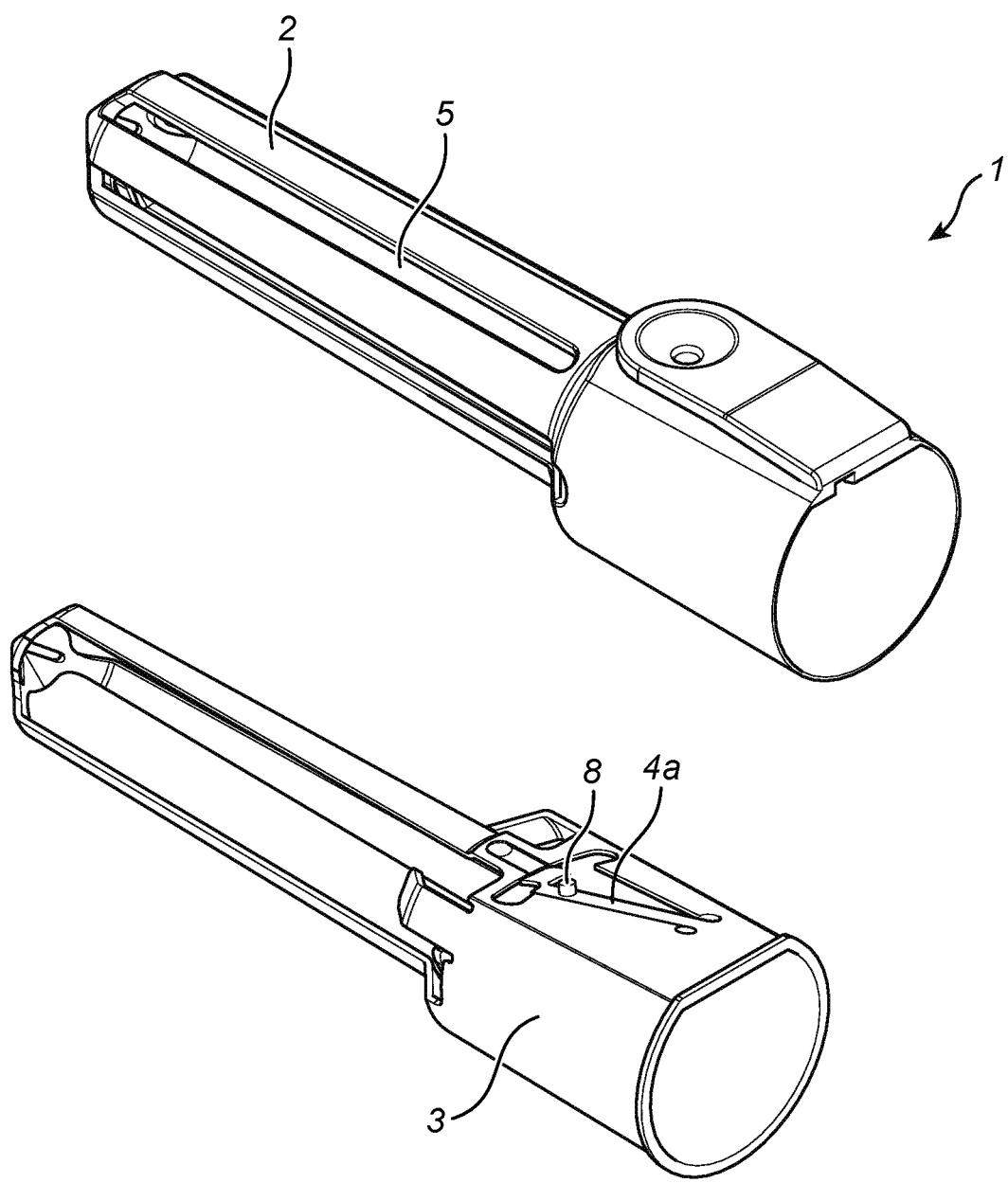

FIG. 2A shows another tip protector device 1 of the present invention comprising a housing 2, through-out holes 5 and a clamping system 3. The clamping system 3 is inserted into the housing 2 and extends within the housing 2. Both parts of the tip protector device 1 are further elucidated in more detail in FIG. 2B. Here the locking element 4a as well as the protruding part 8 is shown. The guiding element (not shown) is similar to the guiding element 4b shown in FIG. 1C. Unlike the locking system 4 of the tip protector device 1 of FIG. 1A-1C, the locking system 4 of the tip protector device 1 of FIG. 2A-2B is designed such that the tip of a medical instrument (not shown), inserted in the tip protector device 1 via arrow P1, is released only by pressing the button 11. By pressing the button 11 the clamping system 3 is partially ejected from the housing 2. The design of the tip protector device 1 is such that by inserting the tip of a medical instrument into the tip protector device 1, the clamping system 3 is moved towards the housing 2 resulting in a clamping force applied onto the tip. By pressing the button 11, the clamping system 3 is ejected and the clamping force is removed to allow easy removal of the tip from the tip protector device.

Again, the protruding part 8 of locking element 4a is designed such that after repeated use of the tip protector device 1 the protruding part 8 is locked by the guiding element (not shown) in a final position. In that particular position, the clamping system 3 is no longer able to move towards the housing 2 and thus unable to clamp the tip of a medical instrument.

Figure 3A:
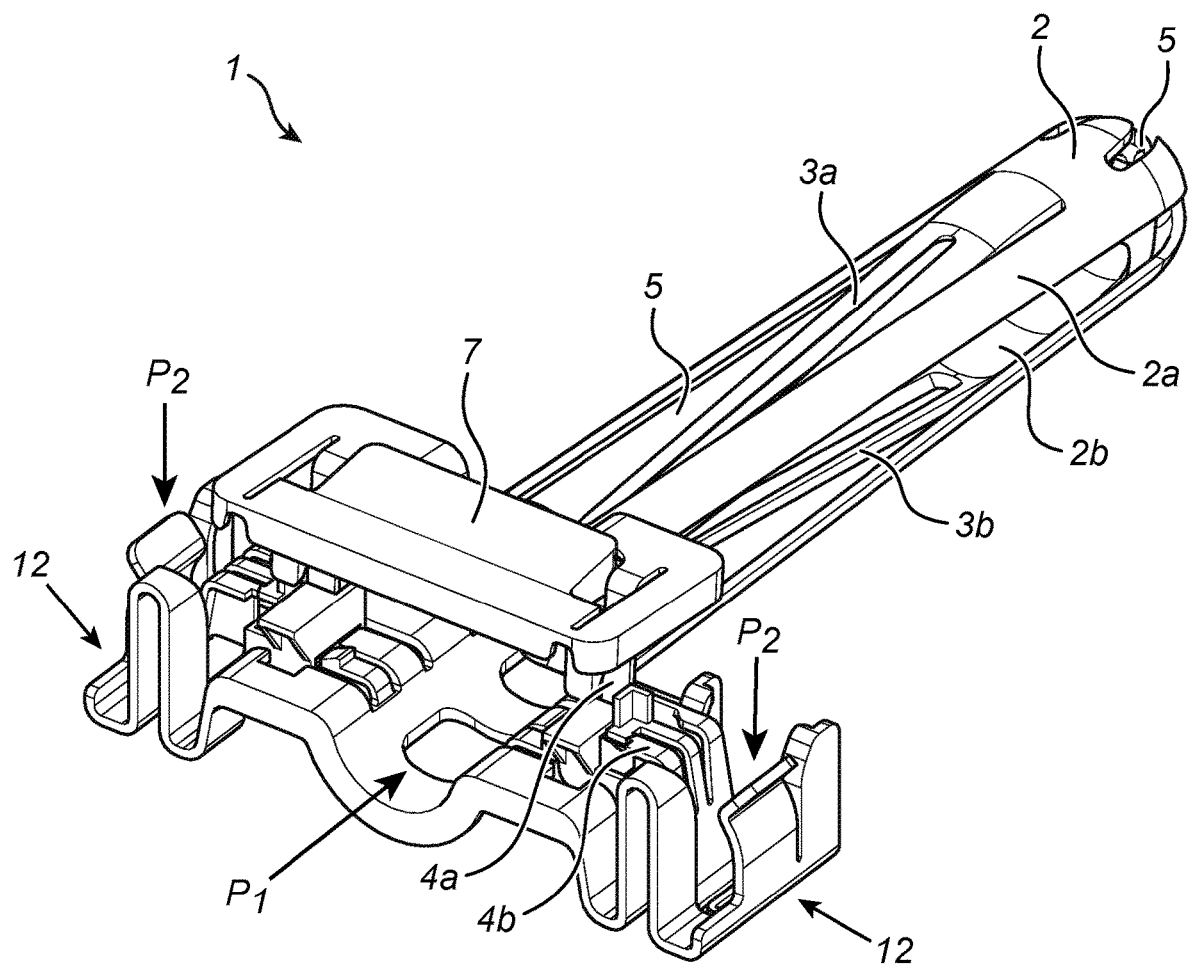
FIG. 3A-3B shows a perspective view of a third embodiment of the tip protector device of the present invention.
Figure 3B:
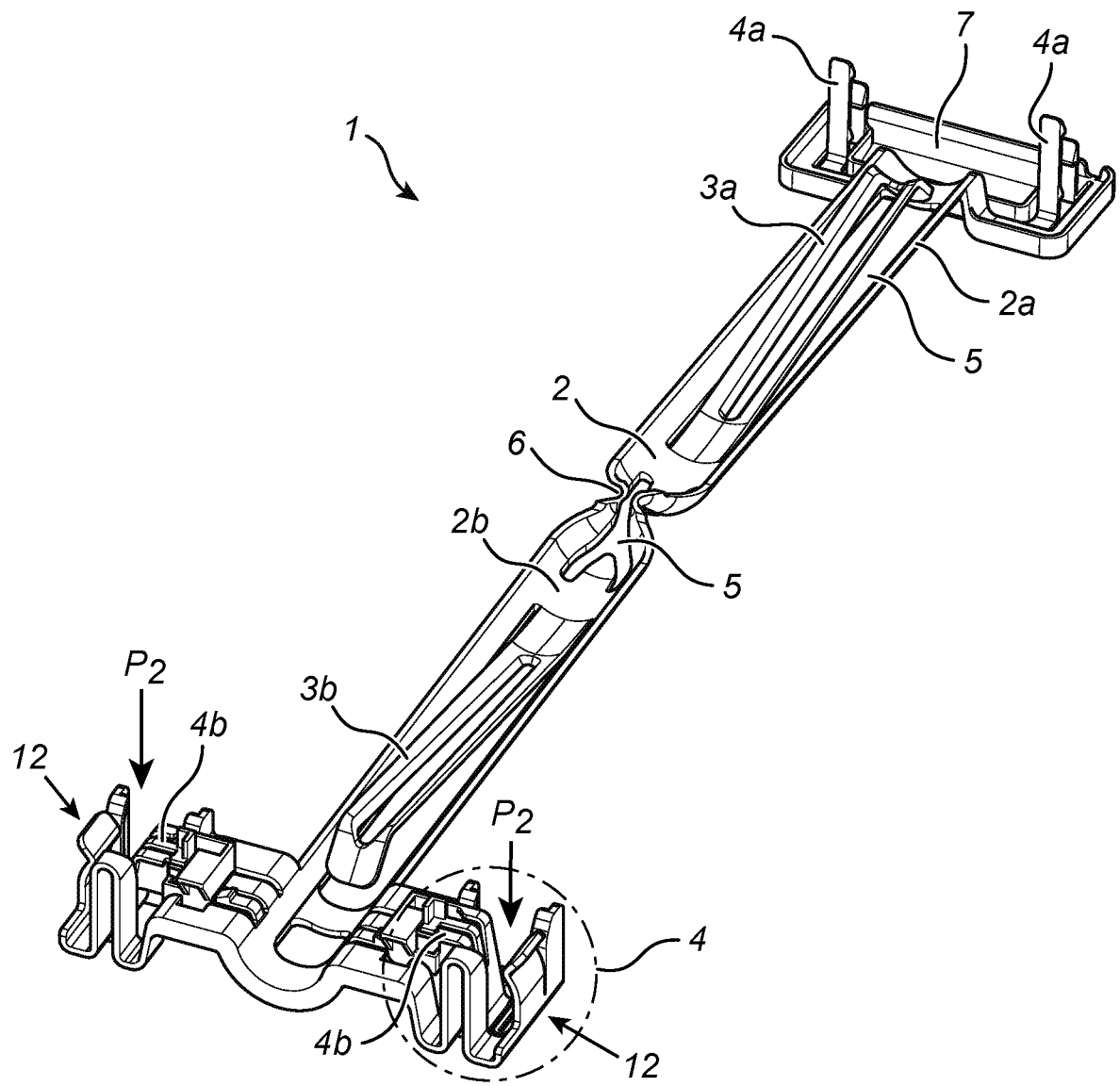

FIG. 3A shows a further embodiment of the tip protector device 1 according to the present invention. The tip protector device 1 comprises a housing 2 including a first housing part 2a and a second housing part 2b wherein both housing parts are provided with large clamping fingers 3a, 3b. The housing 2 is formed from one single piece of material (see: FIG. 3B) comprising a flexible section 6 hingedly connecting the first housing part 2a and the second housing part 2b. The housing 2 is further provided with through-holes 5 and comprises a locking system 4. The locking system includes a click mechanism formed of a locking element 4a and a guiding element 4a. The locking system 4 is activated by insertion of valves (not shown) via arrow P2 into receiving means 12. Once activated, the tip of a medical instrument (not shown) can be inserted via arrow P1 into the tip protector device 1. The tip is clamped by the large clamp fingers 3a, 3b. The click mechanism is further controlled by pressing part 7.

Figure 4A:
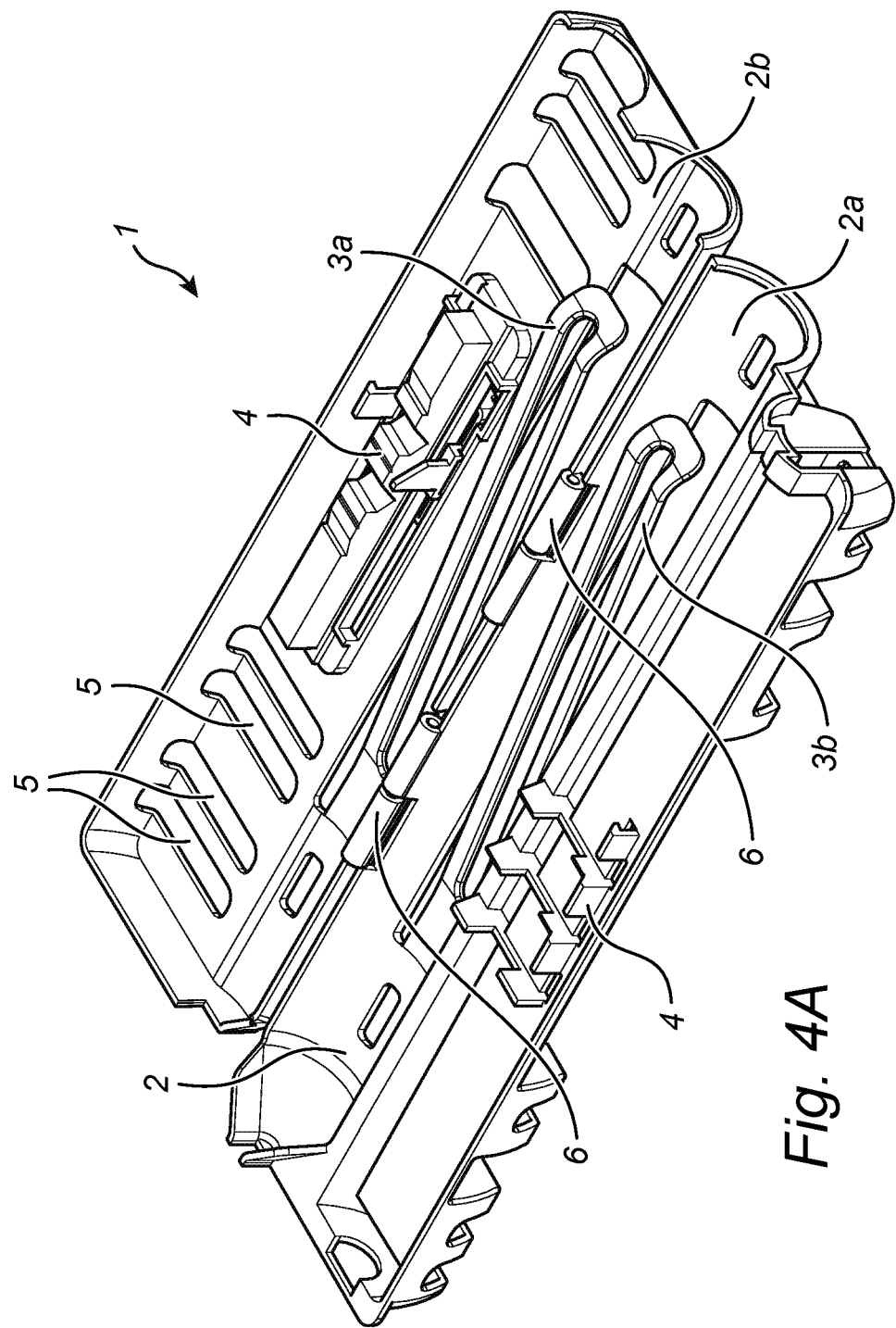
FIG. 4A-4D shows a perspective view of a fourth embodiment of the tip protector device of the present invention.
Figure 4B:
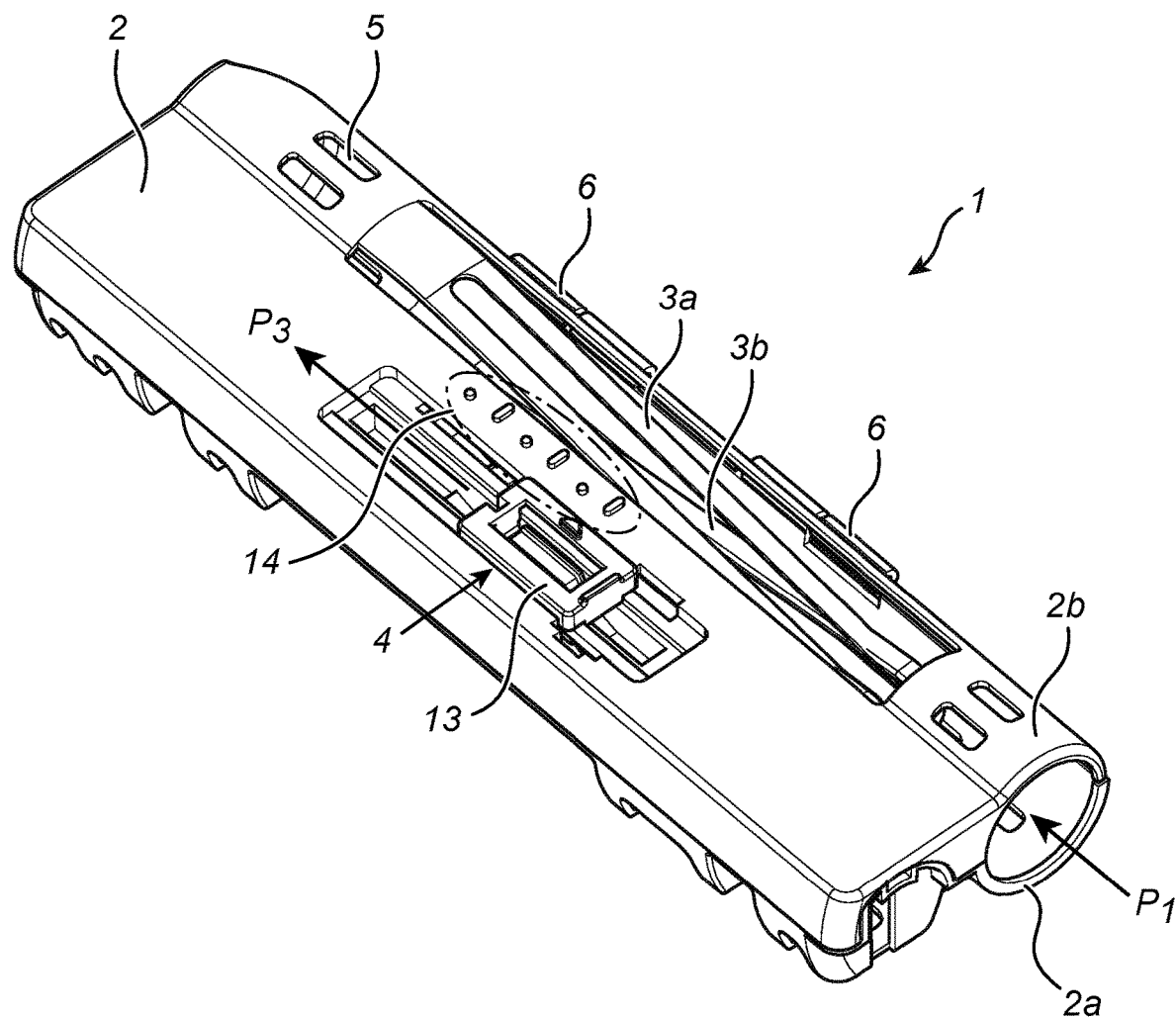

FIG. 4A shows a tip protector device 1 comprising a locking system 4 including a slide switch system. The tip protector device 1 comprises a housing 2 including two housing parts 2a, 2b hingedly connected via hinge 6. Both housing parts 2a, 2b comprising large clamp fingers 3a, 3b. Also, the housing is provided with through-holes 5. The tip of a medical instrument (not shown) may be inserted into one of the housing parts 2a, 2b. Subsequently, the housing parts 2a, 2b are closed to form a closed housing 2 as shown in FIG. 4B. Here the insert of the tip is referred to with arrow P1. Further, the locking system 4 including a slide switch system is further elucidated in more detail. The slide switch system comprises a sliding button 13. The slide switch system is designed such that the sliding button 13 can be moved into one direction only (arrow P3). The locking system 4 further comprising indication means 14 to indicate the status of the tip protector device 1. By the time the sliding button 13 reaches the end of the slide switch system, the tip protector device 1 is in open position and cannot be locked anymore by the user.

Figure 4C:
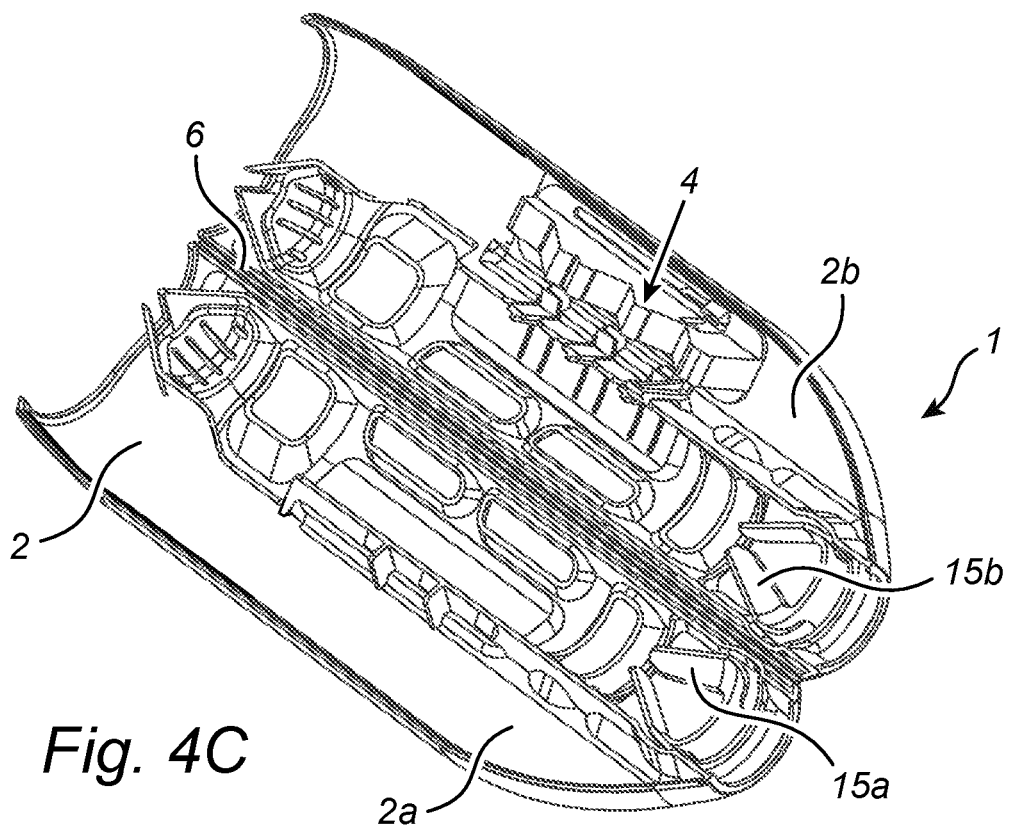
Figure 4D:
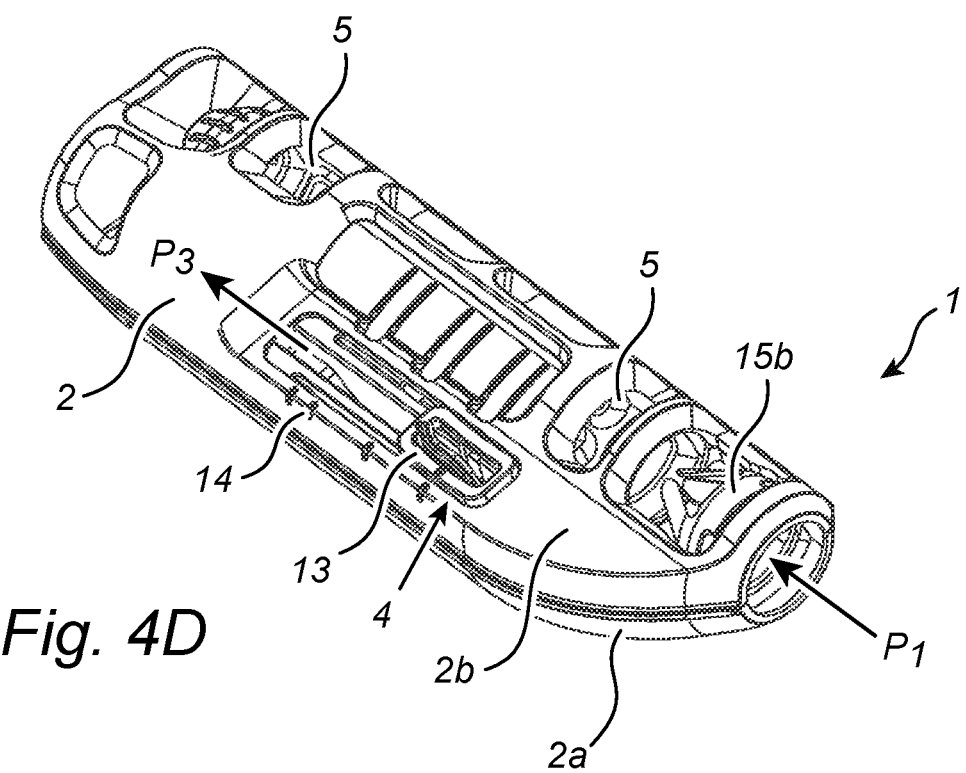
Figure 5A:
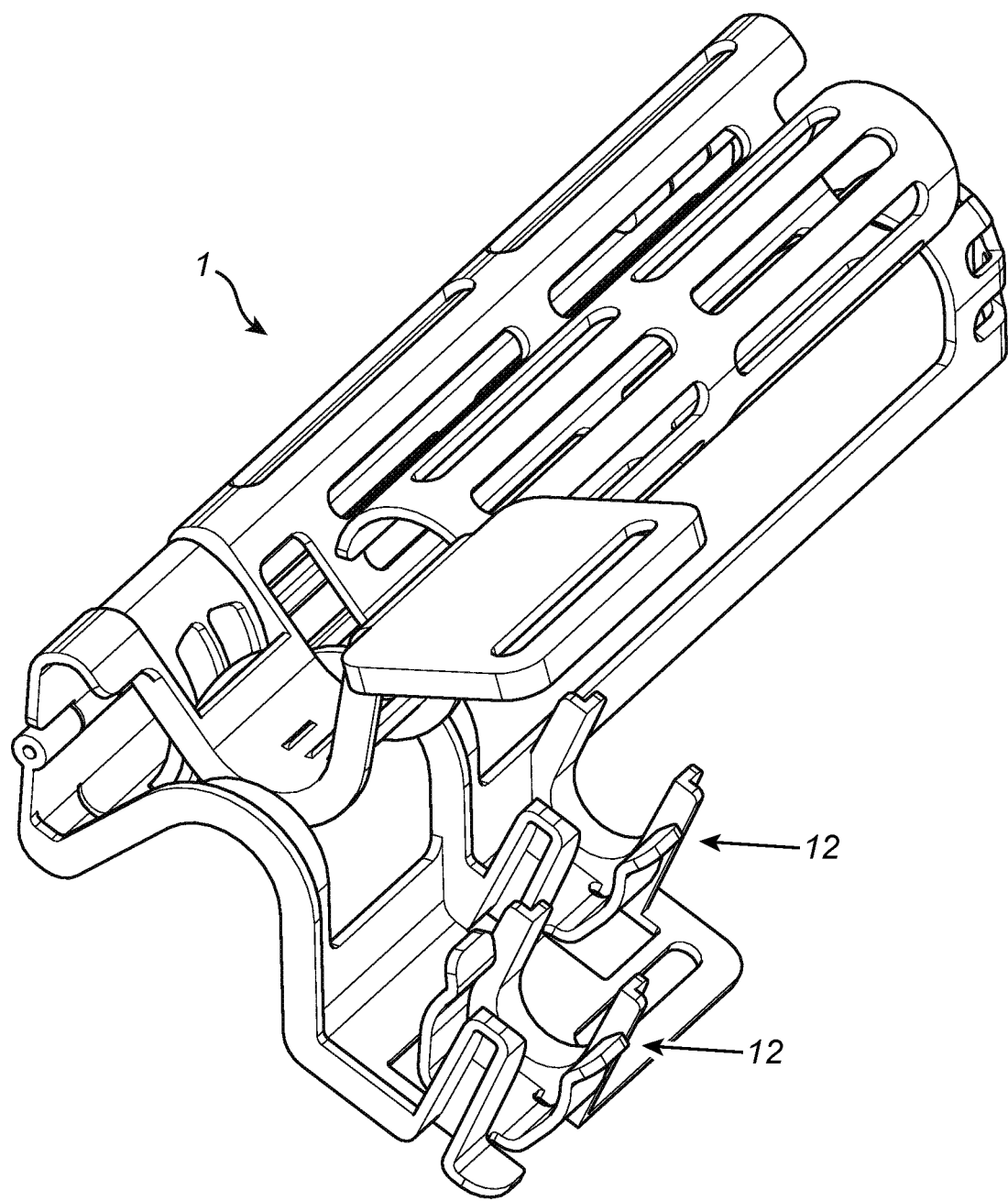
FIG. 5 shows a perspective view of alternative embodiments of the first, second and fourth embodiments of FIGS. 1, 2 and 4.
Figure 5B:
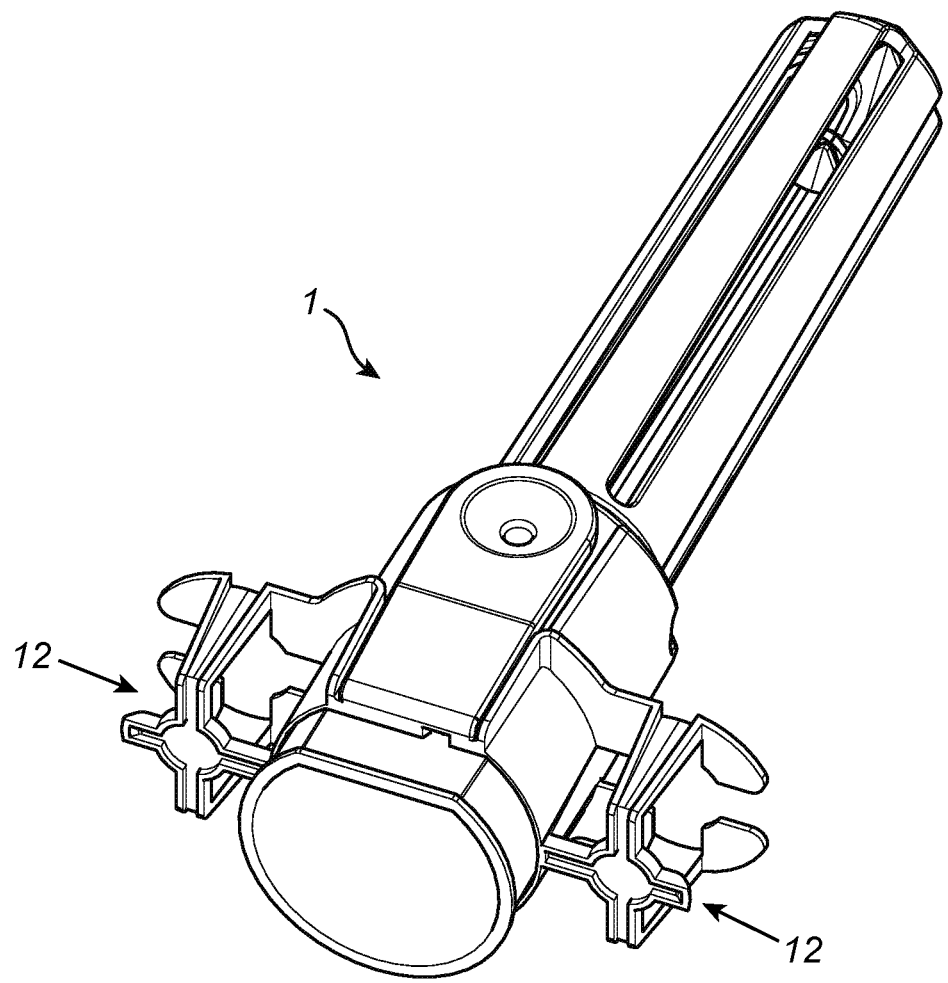
Figure 5C:
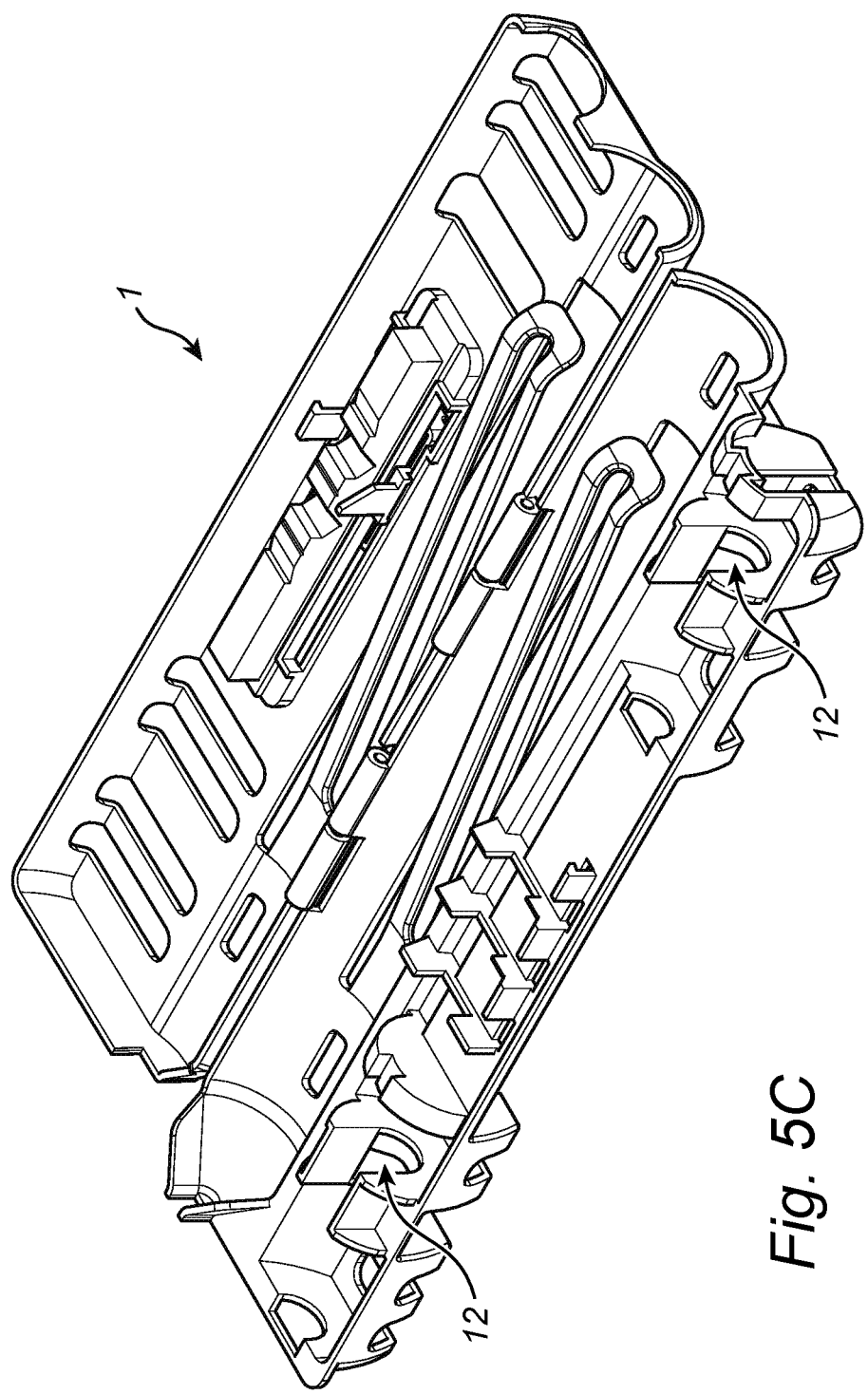
Figure 5D:
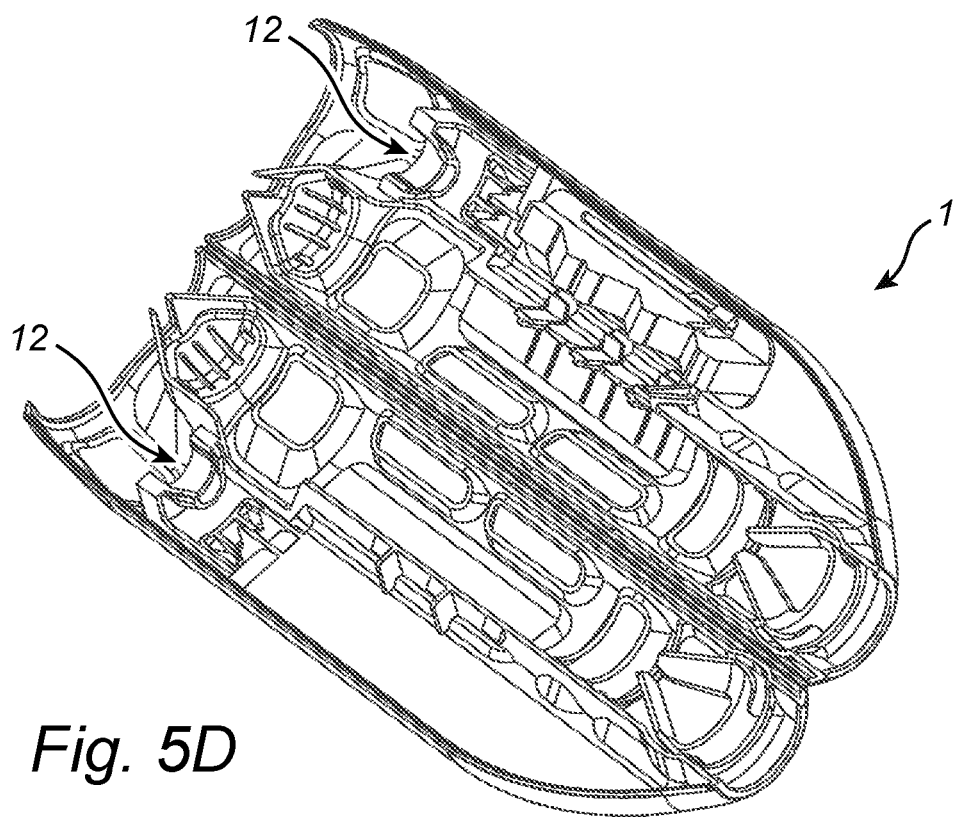
Figure 5E:
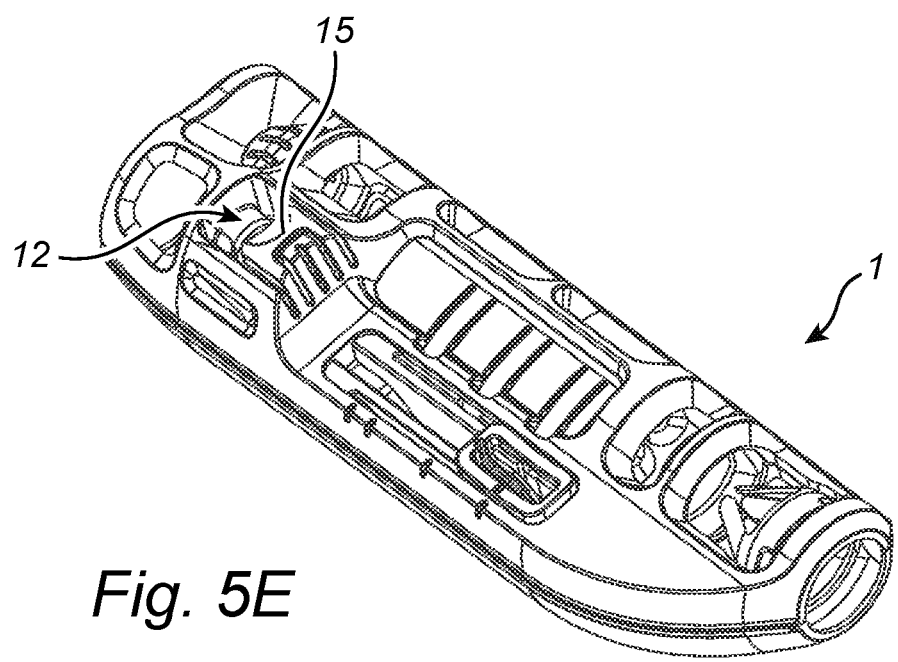

FIGS. 4C and 4D shows further embodiments of the tip protector device 1 shown in FIGS. 4A and 4B. The housing 2 of the tip protector device 1 of FIGS. 4A and 4B is made from one single piece wherein the housing parts 2a, 2b are hingedly connected via weakened line 6. The tip protector device further includes alternative clamping lamellae 15a, 15b.

FIG. 5A-5E shows further embodiments of the tip protector devices 1 of FIGS. 1, 2 and 4 including receiving means 12 for receiving spare parts, such as valves (not shown). With regard to the receiving means 12 of FIGS. 5D and 5E, the tip protector device 1 is provided with disconnecting elements 15 to release the spare part received by the receiving means 12 only by activation of the disconnecting elements 15.

What is claimed is:

1. Tip protector device for a medical instrument comprising:
    a housing configured to releasably receive a tip of a medical instrument;
    a clamping system configured to retain by clamping the tip received by the housing in a retaining position; and
    a locking system configured to perform a locking step, wherein the locking step comprises, successively, the locking and unlocking of the clamping system in the retaining position,
characterized in that the locking system further comprises a blocking element, wherein the blocking element is configured to block the locking system after repeated use of the tip protector device, and in that the locking system is configured to perform at least a first and a second locking step before the blocking element blocks the locking system.

2. Tip protector device according to claim 1, characterized in that the locking system is further configured to perform a third locking step before the blocking element blocks the locking system.

3. Tip protector device according to claim 1, characterized in that the locking system comprises a slide switch system, wherein preferably the slide switch system comprises plural predefined positions, wherein preferably each of the predefined positions provides a locking step or unlocking step.

4. Tip protector device according to claim 1, characterized in that the locking system is configured to manually unlock the clamping system in the retaining position, and/or characterized in that the locking system is configured to manually or automatically lock the clamping system in the retaining position.

5. Tip protector device according to claim 1, characterized in that the clamping system comprises one or more clamping elements wherein preferably the clamping elements cooperate with the housing of the tip protector device and/or characterized in that the clamping system comprises one pair of cooperating clamping elements.

6. Tip protector device according to claim 5, characterized in that the clamping elements retain by clamping the tip under pre-tension and/or wherein the clamping elements comprise flexible clamping lamellae.

7. Tip protector device according to claim 1, characterized in that the housing comprises through-holes and/or characterized in that the housing comprises a cylindrical jacket, the jacket comprising an open end configured to receive a tip of a medical instrument and a closed end located opposite the open end, wherein preferably the closed end comprises through-holes.

8. Tip protector device according to claim 1, characterized in that the tip protector device further comprises at least one receiving means configured to releasably receive at least one spare part of a medical instrument, wherein the at least one receiving means is preferably configured to receive by clamping the at least one spare part.

9. Tip protector device according to claim 8, characterized in that the locking system is configured to, successively, locking and unlocking of the at least one spare part received by the at least one receiving means and/or characterized in that the locking system is configured to perform one or more locking steps only after the at least one receiving means receive at least one spare part.

10. Tip protector device according to claim 8, characterized in that the at least one receiving means comprises a disconnecting element for detaching from the at least one receiving means the at least one spare part coupled with the receiving means, wherein preferably the disconnecting element is further configured to block the at least one receiving means for receiving spare parts of a medical instrument after activation of the disconnecting element.

11. Tip protector device according to claim 1, characterized in that the medical instrument comprises an endoscope.

12. Tip protector device according to claim 8, characterized in that the at least one spare part comprises an endoscope valve.

13. Tip protector device according to claim 1, characterized in that the tip protector device comprises a disposable tip protector device and/or characterized in that the housing is made from a single piece of material, wherein preferably the material is plastic.

14. Tip protector device according to claim 1, characterized in that the housing is formed by:
    a first housing part; and
    a second housing part,
    wherein:
        at least the first housing part or the second housing part comprises the clamping system configured to retain by clamping the tip of a medical instrument received by the housing; and
        the first housing part and the second housing part are hingedly connected to each other.

15. Tip protector device according to claim 14, characterized in that the first housing part and the second housing part comprise the clamping system configured to retain by clamping the tip of a medical instrument received by the housing and/or characterized in that the first housing part and/or the second housing part comprise the locking system configured to perform the locking step.

16. Tip protector device according to claim 14, characterized in that the first housing part and/or the second housing part comprise one or more receiving means, said receiving means are configured to releasably receive at least one part of a medical instrument and/or characterized in that the first housing part and the second housing part are hingedly connected to each other such that both housing parts form the housing under pre-tension.

17. Method for protecting a tip of a medical instrument, comprising the steps of:
    a) providing a medical instrument, such as an endoscope;
    b) providing the tip protector device according to any of the preceding claims;
    c) inserting the tip of the medical instrument in the tip protector device, such that the tip is retained by clamping by the tip protector device in a locked retaining position;

d) unlocking the retaining position and removing the tip from the tip protector device;

e) after use of the medical instrument, inserting the tip of the medical instrument in the tip protector device such that the tip is retained by clamping by the tip protector device in a locked retaining position; and f) unlocking the retaining position and removing the tip from the tip protector device, characterized in that after unlocking the retaining position in step f), the method further comprises discarding the tip protector device in a suitable waste container, with the proviso that the method excludes the step of using the medical instrument within or on the human or animal body.

18. Method according to claim 17, characterized in that the method further comprises, between step c) and step d), transporting the medical instrument, and/or characterized in that the method comprises, in step c) and step e), automatically or manually locking the retaining position.

19. Method according to claim 17, characterized in that the method further comprises, between step b) and step c), washing and disinfecting the medical instrument provided in step a) and the tip protector device provided in step b) and/or characterized in that the method further comprises, between step c) and step d), drying the resulting assembly of step c), said assembly comprising the medical instrument provided in step a) and the tip protector device provided in step b).

20. Method according to claim 17, characterized in that the method further comprises the steps of:

i) providing at least one spare part of the medical instrument provided in step a);

ii) receiving in the tip protector device provided in step b) the at least one spare part provided in step a); and iii) removing in step d) the at least one spare part from the tip protector device, wherein preferably step ii) is performed between step b) and step c) before washing and disinfecting the resulting assembly of step c), said assembly preferably comprising the at least one spare part provided in step i) of the medical instrument provided in step a) and the tip protector device provided in step b).

\* \* \* \* \*